(12) United States Patent
Morgan et al.

(10) Patent No.: US 11,323,840 B2
(45) Date of Patent: May 3, 2022

(54) MICRO-LOCATION MONITORING TECHNIQUES

(71) Applicant: Perfect Sense, Inc., Reston, VA (US)

(72) Inventors: Bryan Morgan, Ramona, CA (US);
Peter Dupris, Hollister, CA (US);
David Gang, Oakton, VA (US)

(73) Assignee: Perfect Sense, Inc., Reston, VA (US)

( * ) Notice: Subject to any disclaimer, the term of this patent is extended or adjusted under 35 U.S.C. 154(b) by 0 days.

(21) Appl. No.: 16/986,752

(22) Filed: Aug. 6, 2020

(65) Prior Publication Data

US 2020/0367011 A1 Nov. 19, 2020

Related U.S. Application Data

(63) Continuation of application No. 16/518,042, filed on Jul. 22, 2019, now abandoned, which is a
(Continued)

(51) Int. Cl.
| | |
|---|---|
| *H04W 4/02* | (2018.01) |
| *H04W 64/00* | (2009.01) |
| *H04W 84/18* | (2009.01) |
| *H04W 24/02* | (2009.01) |
| *H04W 48/12* | (2009.01) |
| *H04W 4/029* | (2018.01) |

(Continued)

(52) U.S. Cl.
CPC ............ *H04W 4/02* (2013.01); *H04B 7/0617* (2013.01); *H04B 7/0626* (2013.01); *H04B 7/0634* (2013.01); *H04B 7/0636* (2013.01); *H04B 7/0697* (2013.01); *H04B 7/12* (2013.01); *H04L 1/04* (2013.01); *H04L 1/06* (2013.01); *H04W 4/027* (2013.01); *H04W 4/029* (2018.02); *H04W 16/24* (2013.01); *H04W 16/32* (2013.01); *H04W 24/02* (2013.01); *H04W 48/12* (2013.01); *H04W 52/00* (2013.01); *H04W 64/00* (2013.01); *H04W 72/04* (2013.01); *H04W 84/18* (2013.01)

(58) Field of Classification Search
CPC ....... H04W 64/00; H04W 48/12; H04W 4/02; H04W 24/02; H04W 84/18; H04W 72/0486; H04W 88/085; H04W 4/025; H04W 88/02; H04W 12/02; H04W 4/008; H04L 5/0048; H04L 5/0032; H04L 63/30; G06Q 10/06313; G06Q 20/327
See application file for complete search history.

(56) References Cited

U.S. PATENT DOCUMENTS

| | | | |
|---|---|---|---|
| 6,529,164 B1 * | 3/2003 | Carter | G01S 5/0036 342/385 |
| 8,199,051 B2 | 6/2012 | Anderson et al. | |

(Continued)

*Primary Examiner* — Fred A Casca
(74) *Attorney, Agent, or Firm* — Fish & Richardson P.C.

(57) ABSTRACT

In some implementations, methods for selecting a set of beacons that are to be monitored by a mobile device may be employed. Specifically, an optimal set of beacons to monitor may be provided to a mobile device depending on particular groups of beacons that are in proximity to the mobile device, the distance from the mobile device to each of the particular groups of beacons, and the mobile device's position/movements as provided by a tracking service such as GPS. These techniques may ensure that the mobile device is not blind to the closest and/or most relevant beacons.

20 Claims, 6 Drawing Sheets

Related U.S. Application Data continuation of application No. 15/850,478, filed on Dec. 21, 2017, now Pat. No. 10,362,437, which is a continuation of application No. 15/299,369, filed on Oct. 20, 2016, now Pat. No. 9,894,475.

(60) Provisional application No. 62/243,993, filed on Oct. 20, 2015.

(51) Int. Cl.
| | |
|---|---|
| *H04B 7/06* | (2006.01) |
| *H04B 7/12* | (2006.01) |
| *H04L 1/04* | (2006.01) |
| *H04L 1/06* | (2006.01) |
| *H04W 16/24* | (2009.01) |
| *H04W 16/32* | (2009.01) |
| *H04W 52/00* | (2009.01) |
| *H04W 72/04* | (2009.01) |

(56) References Cited

U.S. PATENT DOCUMENTS

| | | | |
|---|---|---|---|
| 8,369,242 B2 | 2/2013 | Potkonjak | |
| 8,665,154 B2 | 3/2014 | Lin et al. | |
| 8,810,454 B2 | 8/2014 | Cosman | |
| 8,934,867 B2 | 1/2015 | Shanmugavadivel et al. | |
| 9,485,721 B1 | 11/2016 | Bertz et al. | |
| 2006/0287813 A1* | 12/2006 | Quigley | G01S 5/02 701/533 |
| 2013/0093627 A1* | 4/2013 | Cosman | G01S 19/34 342/451 |
| 2013/0128772 A1* | 5/2013 | Potkonjak | G01S 1/02 370/254 |
| 2014/0233443 A1* | 8/2014 | Kumar | H04L 12/12 370/311 |
| 2016/0094598 A1 | 3/2016 | Gedikian | |
| 2016/0117388 A1* | 4/2016 | Fan | G06F 16/248 717/178 |
| 2016/0242111 A1* | 8/2016 | Wakabayashi | H04W 48/16 |

\* cited by examiner

MICRO-LOCATION MONITORING TECHNIQUES

CROSS-REFERENCE TO RELATED APPLICATION

This application is a continuation of U.S. application Ser. No. 16/518,042, filed Jul. 22, 2019, now pending, which is a continuation of U.S. application Ser. No. 15/850,478, filed Dec. 21, 2017, now U.S. Pat. No. 10,362,437, which is a continuation of U.S. application Ser. No. 15/299,369, filed Oct. 20, 2016, now U.S. Pat. No. 9,894,475, which claims priority from U.S. Provisional Application No. 62/243,993, filed Oct. 20, 2015, and titled "MICRO-LOCATION MONITORING TECHNIQUES," all of which is hereby incorporated by reference in its entirety.

TECHNICAL FIELD

This application generally relates to wireless communications, and more particularly to position tracking of mobile devices using wireless beacons.

BACKGROUND

Beacons using wireless personal area network technology can be used to precisely identify the locations of nearby electronic devices. A business may install thousands of beacons across a large geographical area in order to track locations of electronic devices within the area.

SUMMARY

Many mobile devices are often limited in their ability to concurrently monitor a number of incoming wireless connections in order to preserve battery life. For instance, an operating system of a mobile device may specify a threshold number of wireless beacons that can be simultaneously monitored by the mobile device at any one instance. However, when a mobile device is in a location that has many beacons, a number of beacons that are potentially detectable by the mobile device can be greater than a threshold number of connections available for the mobile device. As a result, in these scenarios, many mobile devices are unable to process data from nearby beacons because they are not being actively monitored.

In some implementations, systems and methods are capable of performing micro-location monitoring techniques that enable a mobile device to selectively adjust the monitoring of beacons based on the movement of the mobile device within a location. The adjustments can be performed such that the total number of beacons being monitored by the mobile device at any instance is below a specified threshold associated with the mobile device. For example, a location can include groups of beacons that are each associated with different geographical areas within the location. In response to detecting a movement of the mobile device between different geographical areas, a set of nearby beacons within a new geographical area can be identified by an associated server. The mobile device can then scan for information broadcast by the identified set of nearby beacons while disabling monitoring of beacons that are associated with the old geographical area.

The micro-location monitoring techniques described throughout can be also be used to provide area-specific (or position-specific) content for output on the mobile device. For instance, beacons can be placed in a predetermined array such that the physical position of individual beacons within the location corresponds to areas of interest within the location. The server may store data that associates each individual beacon with a set of electronic content that is relevant to the corresponding areas of interest within the location. As an example, beacons may be placed in different departments of a store, and the server may store data that maps each of the beacons to content associated with different products that are available for purchase in the corresponding departments of the store.

In response to detecting movement of the mobile device between different geographical areas (e.g., departments) within a location (e.g., department store), connection events between the mobile device and individual beacons within the location can then be used to provide relevant area-specific content associated with the beacon for output on the mobile device. In this regard, the micro-location monitoring techniques can be used to dynamically adjust content displayed on the mobile device based on movements detected based on connection events with individual beacons within the location.

In some aspects, the subject matter described in this specification may be embodied in methods that may include the actions of: determining, by a mobile device, that the mobile device has moved from a first geographical area to a second geographical area; in response to determining that the mobile device has moved from the first geographical area to the second geographical area, sending, by the mobile device and to a server, a request to send the mobile device identification information that identifies beacons associated with the second geographical area; receiving, by the mobile device from the server, identification information that identifies a particular set of beacons within the second geographical area; and in response to receiving the identification information that identifies the particular set of beacons associated with the second geographical area, scanning, by the mobile device, for information that is being broadcast by the particular set of beacons.

One or more implementations may include the following optional features. For instance, in some implementations, determining that the mobile device has moved from the first geographical area to the second geographical area includes the actions of: obtaining data indicating at least (i) a present position of the mobile device within the first geographical area, and (ii) a predicted direction of movement of the mobile device within the first geographical area; and determining that the mobile device has moved from the first geographical area to the second geographical area based on the obtained data indicating the present position of the mobile device within the first geographical area, and the predicted direction of movement of the mobile device within the first geographical area.

In some implementations, the method further includes the actions of: obtaining, by the mobile device, sensor data indicating respective signal connection strengths for one or more beacons that are associated with the second geographical area and are currently being monitored by the mobile device; and determining a predicted position for the mobile device within the second geographical area based at least on the respective signal connection strengths for the one or more beacons that are associated with the second geographical area and are being currently monitored by the mobile device.

In some implementations, the request to send the mobile device identification information that identifies beacons associated with the second geographical area identifies a predicted position of the mobile device within the second geographical area, and the identification information that identifies the particular set of beacons are determined by the server to be with a proximity to the predicted position of the mobile device within the second geographical area.

In some implementations, the method further includes the actions of disabling, by the mobile device, existing wireless monitoring of one or more beacons that are associated with the first geographical area; and enabling, by the mobile device and based on the identification information of the particular set of beacons, wireless monitoring of one or more beacons that are included in the second geographical area such that a total number of beacons monitored by the mobile device is below a threshold number of beacons for the mobile device.

In some implementations, determining that the mobile device has moved from a first geographical area to the second geographical area includes: determining that the mobile device has exited a geographical boundary specified by a first geo-fence associated with the first geographical area; and determining that the mobile device has entered a geographical boundary specified by a second geo-fence associated with the second geographical area.

In some implementations, the method further includes the actions of: after determining that the mobile device has moved from a first geographical area to a second geographical area, identifying one or more beacons from among the particular set of beacons that are within a physical proximity to a predicted position of the mobile device within the second geographical area; determining, for at least one of the one or more identified beacons, a time period for which the at least one identified beacon remains within the physical proximity to the predicted position of the mobile device within the second geographical area.

In some implementations, the identification information that identifies the particular set of beacons received from the server specifies (i) a physical arrangement of the particular set of beacons within the second geographical area, and (ii) for each beacon within the particular set of beacons, a unique identifier for a particular beacon, and electronic content associated with the particular beacon.

In some implementations, scanning for information that is being broadcast by the particular set of beacons includes the actions of: identifying a particular beacon from among the particular set of beacons that is determined by the mobile device to be closest to the mobile device; and providing, for output on the client device, the electronic content associated with the particular beacon.

In some implementations, the electronic content associated with the particular beacon includes an advertisement for a product placed in a position within the second geographical area, the position of the product corresponding to the position of the particular beacon within the physical arrangement of the particular set of beacons within the second geographical area.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

Other implementations of this and other aspects include corresponding methods, apparatus, and computer programs, configured to perform the actions of the systems, encoded on computer storage devices.

The details of one or more implementations are set forth in the accompanying drawings and the description below. Other features will be apparent from the description and drawings, and from the claims.

DETAILED DESCRIPTION

Figure 1:
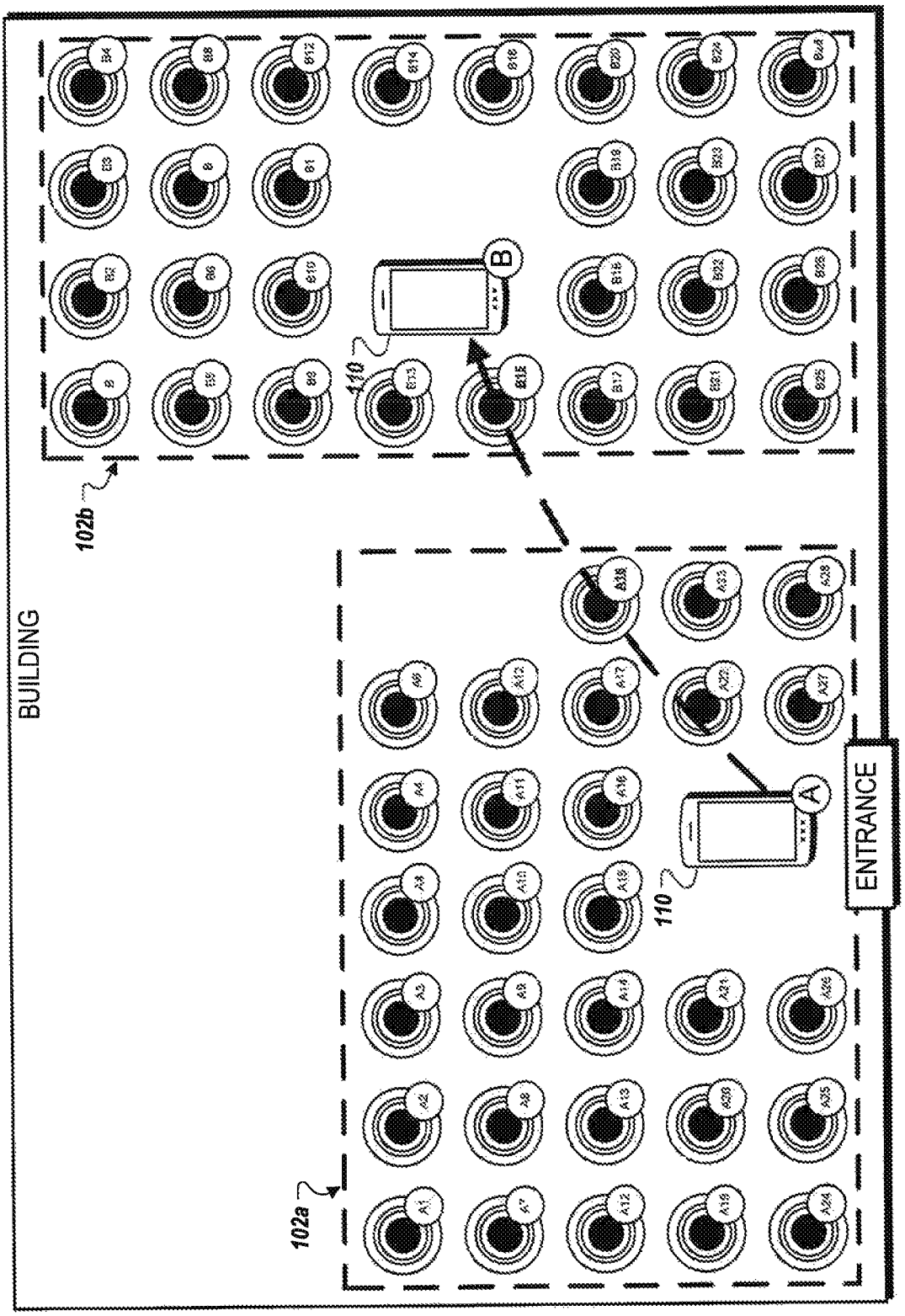
FIG. 1 illustrates an example of a micro-location monitoring technique for a mobile device.

In general, systems and methods described throughout are capable of performing micro-location monitoring techniques that enable a mobile device to selectively adjust the monitoring of beacons based on the movement of the mobile device within a specified location. The adjustments can be performed such that the total number of beacons being monitored by the mobile device at any instance is below a specified threshold associated with the mobile device. For example, a location can include groups of beacons that are each associated with different geographical areas within the location. In response to detecting a movement of the mobile device between different geographical areas, a set (e.g., a list) of nearby beacons within a new geographical area can be identified by an associated server. The mobile device can then scan for information broadcast by the identified set of nearby beacons while disabling monitoring of beacons that are associated with the old geographical area.

As described throughout, a "beacon" refers to any type of electronic device that is capable of broadcasting or announcing the presence of a wireless communication signal to nearby electronic devices such as mobile devices. In some instances, the beacons are capable of using Bluetooth Low Energy (BLE) to transmit wireless signals over short distances while maintaining low energy consumption and cost. The wireless signals broadcasted by the beacons can include self-contained packets of data that can be collected by a mobile device and used to trigger actions to be performed on the mobile device (e.g., push messages, app actions, and prompts). Signals transmitted by the beacons can have a specified broadcast range (e.g., 100 meters) and/or broadcast intervals (e.g., 100 ms). In addition, signals transmitted by the beacons can also include unique beacon identifiers that enable the mobile device to identify the presence of individual beacons in the presence of multiple beacons. Beacons may be implemented within retail environments to provide offers to mobile devices for nearby products as users walk through a store.

As described throughout, a "position" (or a "micro-location") refers to a point within a geographical area included within a location that corresponds to a physical placement of either a beacon or a mobile device. A position of a beacon can be used as a reference to infer a predicted position of a mobile device within the location. In some implementations, the position of the mobile device is predicted based on a combination of detecting broadcast signals of nearby beacons, identifying the physical arrangement of the nearby beacons within the location, and determining the respective signal strengths of each of the broadcast signals to pinpoint a location of the mobile device relative to each of the beacons. For example, beacons may be arranged in certain axial arrangements such that the respective signal strengths of beacons placed in a linear arrangement can be used to identify a location of the mobile device along an axis defined by the linear arrangement. In another example, beacons may be placed in a grid arrangement such that respective signal strengths measured for nearby beacons can be used to identify a coordinate location of the mobile device within the location.

As described throughout, a "broadcast range" refers to a geographical area surrounding a physical position of a beacon in which the beacon is detectable by a mobile device when located within the geographical area. The broadcast range of the beacon is determined by its broadcast power, which determines how far a mobile device can be from the beacon and still detect the broadcast signal advertised by the beacon. For example, a beacon can have a broadcast power ranging from −40 decibel-milliwatts (dBm) to +4 dBm, which enables a corresponding broadcast range between 40 to 50 meters. Broadcast ranges of two or more beacons may overlap if the physical positions of the beacons are close enough such that the detectable geographical areas of the beacons include overlapping regions. If a mobile device is located within an overlapping region for multiple beacons, then it is "within" the broadcast ranges for each of the multiple beacons, and as a result, is capable of detecting the respective broadcast signals of each individual beacon.

As described throughout, a "connection event" refers to a time point associated with either a detection, or a loss, of a beacon's broadcast signal as a mobile device either enters into, or exits out of, a broadcast range of the beacon. For example, a connection event can be triggered at a time point when a mobile device moves into a broadcast range, and as a result, detects a broadcast signal of the beacon. In another example, a connection event can be triggered for a time point when a mobile device exits a broadcast range, and as a result, loses the ability to detect a broadcast signal of the beacon. As described in more detail below, in some implementations, connection events relating to both the detection of, and the loss of, a broadcast signal can be measured to determine a time frame in which the mobile device was located within the broadcast range of a particular beacon.

As described throughout, "physical proximity" (or "proximity") between a beacon and a mobile device refers to a determination that the distance between the two devices satisfies a predetermined threshold distance. For example, a mobile device can be determined to be within a proximity to a beacon if a detected signal strength of the beacon's broadcast signal exceeds a predetermined signal strength. The threshold associated with the physical proximity can be adjusted in order to adjust a sensitivity by which a mobile device is determined to be within a proximity to a beacon. For example, if beacons are densely arranged within a particular geographical area, then the threshold can be set to a high value in order to reduce the likelihood of the mobile device being determined to be within a proximity to multiple beacons when located in a specified position within the geographical area. In some implementations, the specified threshold to determine that the mobile device is within a proximity to a particular beacon may vary based on the physical position of the beacon within a location.

For context, in some implementations, the micro-monitoring techniques described in the figures below can be initiated when an application running in the background of a mobile device determines that the mobile device has entered into, or crossed some virtual boundary associated with, a specified location that includes beacons that broadcast signals that are detectable by the application. This determination can be based on using location data of the mobile device such as GPS data or data indicating that the mobile device has recently crossed a geo-fence associated with the specified location.

When the mobile device enters the specified location, beacons within the specified location can exchange communications with the application, which then exchanges communications with an application server that is associated with the application on the mobile device and the specified location that includes the beacons. In response to determining by the application that the mobile device has entered the specified location, the application then automatically transmits a request for beacon identification information from the application server, which stores location-specific reference information for the beacons in the specified location (e.g., a predetermined arrangement of beacons within the location, broadcast signal information for each of the beacons within the location, groupings of individual beacons within the location). The application server then transmits the beacon identification information to the mobile device in order to configure the application to detect and identify broadcast signals for beacons within a detectable region (e.g., beacons that have a broadcast range that is detectable by the mobile device at a particular location).

However, as described above, in certain circumstances, mobile devices may have a specified limit on a number of beacons that can be simultaneously monitored by the application at any particular instance. For example, an operating system of the mobile device may specify that only twenty beacons can be simultaneously monitored even though greater than twenty beacons are detectable by the monitoring device. In such circumstances, the micro-location monitoring techniques discussed in the figures below enable the application to intelligently and selectively monitor specific subsets of beacons based on ongoing communications between the mobile device and the application server associated with the placement of the beacons placed within the location. Such techniques can optionally be used for the selective provisioning of electronic content for output on the mobile device based on the monitoring of the beacons as described in more detail below.

Figure 2:
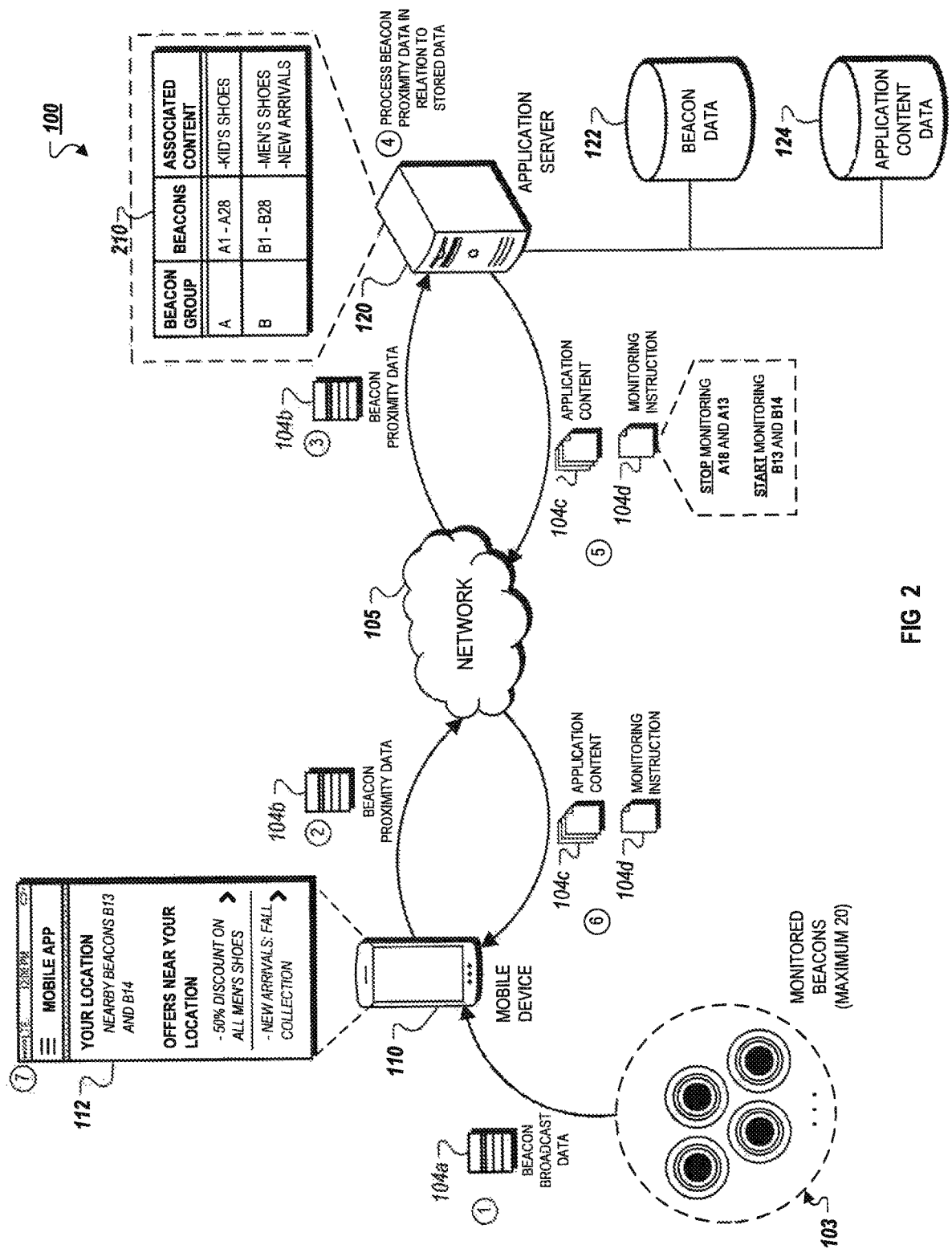
FIG. 2 illustrates an example of a system that is capable of performing micro-location monitoring techniques for a mobile device.
Figure 3A:
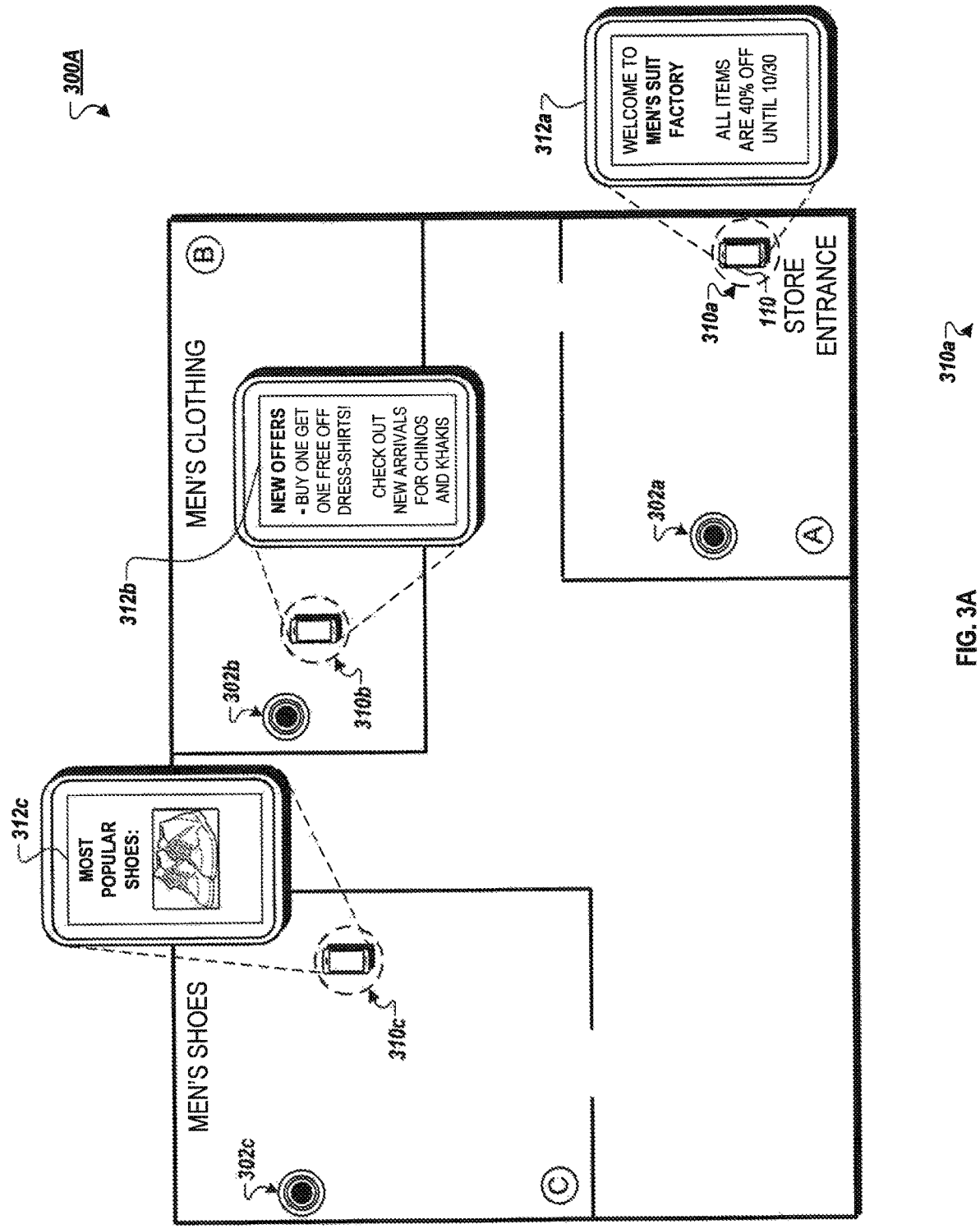
FIGS. 3A-3B illustrate examples of micro-location monitoring techniques for a mobile device.
Figure 3B:
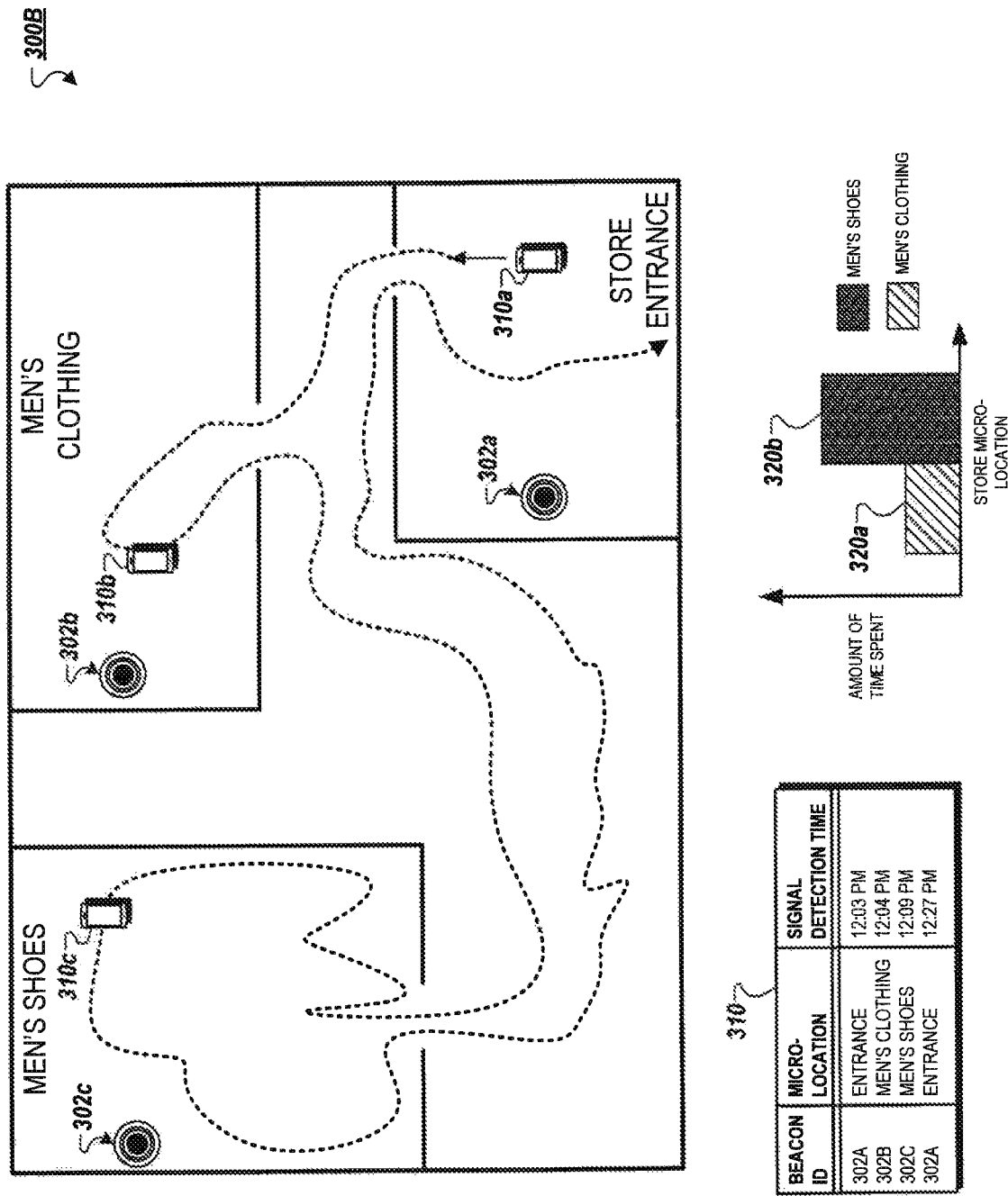

Generally, the micro-location monitoring techniques illustrated in the figures below can represent alternative techniques, which can involve, for example, different arrangements, configurations, and/or specifications for the beacons used with each technique. For example, FIGS. 1 and 2 illustrate a technique in which a detected movement of a mobile device relative to a pre-determined arrangement of beacons is used to selectively monitor particular subsets of beacons within the location in relation to the detected movement of the mobile device. Application content can also be selectively provided for output on the mobile device based on the detected movement. FIG. 3A illustrates a technique that extends from the techniques illustrated in FIGS. 1 and 2 by placing individual or multiple beacons in different areas of a location and associating the beacons in different areas with different types of content. FIG. 3B finally illustrates a technique that extends from the technique illustrated in FIGS. 1 and 2 using specific position tracking of the mobile device to identify a waypoint of the user through a location based on connection events between the mobile device and different beacons at different time points, among other types of signals.

FIG. 1 illustrates an example of a micro-location monitoring technique for a mobile device 110. More particularly, the figure illustrates an array of beacons that are physically arranged within different geographical areas inside of a building. In this example, beacons within the location are arranged in two distinct groups (e.g., group of beacons 102a and 102b), each of which include 28 individual beacons. The beacons included in group 102a includes beacons A1-A28, and the beacons included in group 102b includes beacons B1-B28.

In this example, the mobile device 110 is configured to be capable of only monitoring twenty beacons simultaneously at any given regardless of the number of deacons that are potentially detectable because the mobile device is within their broadcast range. For instance, when the mobile device 110 enters the building through the entrance, the mobile device 110 is initially located at a position that is indicated with the letter "A" (referred hereinafter as "position A"). The mobile device 110 can then move to an updated position that is indicated with the letter "B" (referring hereinafter as "position B"). In either of these positions, the mobile device 110 may be located within the broadcast ranges of all of the beacons within the building (e.g., beacons A1-A28 and beacons B1-B28), or some of the beacons within the building (e.g., a particular subset of the group of beacons 102a, and another particular subset of the group of beacons 102b). Regardless of the number of beacons that have broadcast ranges that include the mobile device 110, the maximum number of beacons that are actually monitored (and hence, actually detected) by the mobile device 110 cannot exceed twenty beacons.

As the mobile device 110 moves within the building (e.g., from position A to position B), the broadcast ranges of some beacons may fall outside the position of the mobile device 110, while the broadcast ranges of other beacons may include the updated position of the mobile device 110. As an illustration, beacons A24 and A25 in the figure may have broadcast ranges that only include position A, while the beacons B27 and B28 may have broadcast ranges that only include position B. Thus, as the mobile device 110 moves between position A and position B, the beacons A24 and B25 become undetectable, whereas beacons B27 and B28 can potentially become detectable (assuming that the beacons B27 and B28 are one of the potentially detectable beacons that are actually included within the twenty beacons that are simultaneously monitored by the mobile device 110 when it is located in position B).

However, in other instances where the beacons are densely arranged within a location, each of the beacons A1-28 and the beacons B1-B28 may be potentially detectable within an entire area encompassing the location (e.g., an area encompassing the entire building) such that as the mobile device 110 moves from position A to position B, the change in position does not change the number of beacons that have a broadcast range that includes a current position of the mobile device 110. These instances, however, can be problematic because although the position of the mobile device 110 has changed (e.g., from position A to position B), the beacons that are actually monitored when the mobile device 110 is located in an updated position (e.g., position B) can still include beacons that were initially detected and monitored by the mobile device 110 when the mobile device was located in position A (because the detectability of these beacons has not changed since both positions A and B are included within the broadcast regions of the beacons). In such instances, the location monitoring techniques described in FIG. 2 below, can be used to enable the mobile device 110 to exchange communications with an application server that provides instructions to adjust the selective monitoring of particular subsets of beacons in relation to a detected movement of the mobile device 110.

The general area (e.g., a geographical area that includes the present position of the mobile device 110) of the mobile device 110, and the movement of the mobile device 110 between positions (e.g., between positions included in different geographical areas) can be computing using a variety of techniques. In some instances, GPS data can be used to estimate a general area in which the mobile device 110 is located (e.g., inside a location that includes beacons). In other instances, sensor data of the mobile device 110 can be used to identify the area and the movement of the mobile device 110. For example, inertial measurements by an accelerometer of the mobile device 110 and/or magnetic fields measured by a compass of the mobile device 110 in relation to the last known GPS signal of the mobile device 110 can be used to infer an estimated position within the building in relation to its position near the outside of the location. In other examples, as described in more detail with respect to FIGS. 3A and 3B, the system enables more precise position tracking techniques using communications with the beacons within the location (e.g., identifying connection events between individual reference beacons, combining connection event data with Wi-Fi transceiver data, using respective connection strengths of individual beacons in relation to a predetermined array of beacons, etc.).

The mobile device 110 described in association with FIG. 1 may include, for example, one or more of mobile computing devices, personal digital assistants (PDAs), cellular telephones, smartphones, tablet computing devices, laptop computing devices, electronic wearable devices, among other types of electronic devices. The beacons described in association with FIG. 1 may broadcast packets of data that include respective identification information using short-range radio or light techniques such as BLE or infrared communication. The mobile device 110 can also communicate with one or more other computing devices, such as a remote server, over a network. In some implementations, the mobile device 110 may communicate with one or more other computing devices over one or more networks, such as a local area network, a wide area network, and/or the Internet. One or more of the networks in the network may be wireless, such as a cellular telephone network or a Wi-Fi network. The beacons, the mobile device, and the one or more computers make up a system 100 described in greater detail below with respect to FIG. 2.

In some implementations, identification of the group of beacons 104b can be based additionally or alternatively on other types of data other than communication between the mobile device 110 and the beacons illustrated in FIG. 1. For instance, the group of beacons, which are designated by the reference numerals 102a and 102b in FIG. 1, can be determined based on global positioning system (GPS) data associated with the mobile device 110, wireless connectivity data of the mobile device 110, cellular data of the mobile device 110, or a combination of such. In such instances, such data can be used to independently identify a location of the mobile device 110 in order to verify movement detection of the mobile device 110 based on the connection events with individual beacons. For example, changes to detected Wi-Fi signal strengths by the mobile device 110, indicated by a received signal strength indicator (RSSI) value, can be used, along with a known location of one or more corresponding Wi-Fi transceivers, to determine if the mobile device 110 is moving in a certain direction. In another example, changes to GPS location data can also be used to indicate movements of the mobile device 110.

In some implementations, movements of the mobile device 110 can be determined based on the use of geo-fences and/or other types of virtual perimeters that are associated with collections of beacons, such as the collections of beacons 102a and 102b shown in FIG. 1. In such implementations, a geo-fence may define a specific geographical area within the location and may be associated with each of the beacons that are encompassed within the specific geographical area. The geo-fence can then monitor the movement of the mobile device 110 in relation to the specific geographical area. In one example, in response to determining that the mobile device 110 has recently traversed a virtual boundary specified by a first geo-fence, the mobile device 110 can then determine that the mobile device 110 has entered into the geographical area defined by the virtual boundary of the first geo-fence. The mobile device 110 can then automatically determine a group of beacons to begin monitoring based on their association with the first geo-fence. Using the same techniques, the mobile device 110 can also automatically determine a group of beacons to stop monitoring based on their association with a second geo-fence that the mobile device 110 recently traversed in order to exit a corresponding geographical area defined by the second geo-fence's virtual boundary.

FIG. 2 illustrates an example of a system 100 that is capable of performing micro-location monitoring techniques for the mobile device 110 illustrated in FIG. 1. The system 100 generally includes monitored beacons 103, the mobile device 110, and an application server 120 connected over a wireless network 105. The monitored beacons 103 includes all beacons within a location that are actually monitored by the mobile device 110 when it is located at position A. For example, as described above, the monitored beacons 103 can include a combination of beacons from groups 102a and 102b or only beacons from group 102a depending on the particular detection used by the mobile device 110 (if the number of potentially detectable beacons exceeds the twenty beacons which the mobile device 110 can monitor at any position). The mobile device 110 includes an application 112 provided for output on the display of the mobile device 110. The application server 120 remotely stores various types of data such as beacon data 122 for the group of wireless beacons 103 and application content data 124 to be provided on the application 112. The beacon data 122 can include reference data for the location that specifies, for example, a predetermined arrangement for all beacons within the location, groupings of beacons among all beacons (e.g., groups 102a and 102b), or content mappings between individual beacons (or groups of beacons) and corresponding content within the application content data 124 that is mapped to the individual beacons (or groups of beacons).

In general, the communication between the monitored beacons 103, the mobile device 110, and the application server 120 enables the mobile device 110 to selectively and intelligently monitor a particular set of beacons within the location in relation to a detected movement of the mobile device 110 in order to more accurately and precisely monitor a group of beacons that is more relevant to updated position of the mobile device 110 (e.g., the position B) after it has moved from an initial position (position A).

As a brief illustration, the mobile device 110 initially obtains beacon broadcast data 104a for the monitored beacons 103. In response to a detected movement of the mobile device 110, the obtained beacon broadcast data 104a is then included within the beacon proximity data 104b, which is transmitted by the mobile device 110 to the application server 120 over the network 105. The identification information for the beacons (e.g., beacon identifiers associated with the monitored beacons 103) are then processed by the application server 120 alongside data contained within the reference beacon data 122 and application content data 124 to identify (i) a particular set of beacons to monitor based on the detected movement, and (ii) application content associated with at least some of the beacons included within the particular set of beacons. The identified information is then provided back to mobile device 110 as application content 104c and a monitoring instruction 104d over the network 105. The mobile device 110 then adjusts the monitoring of beacons within the location based on the monitoring instruction, and provides content specified by the application content 104c for output on the application 112.

In more detail, with respect to step (1), which is depicted in FIG. 2 using the label "1," the mobile device 110 initially obtains beacon broadcast data 104a associated with the monitored beacons 103. The beacon broadcast data 104a can include a unique identifier that is associated with each individual beacon within the monitored beacons 103. The mobile device 110 detects the beacon broadcast data 104a for the monitored beacons 103 when located the mobile device 110 initially enters the location (e.g., when located in position A). The monitored beacons 103 includes twenty beacons from among the among the group of beacons 102a and the group of beacons 102b within the location illustrated in FIG. 1. In some instances, the monitored beacons 103 includes a subset of the group of the beacons 102a and another subset of the group of beacons 102b (e.g., fifteen beacons from group 102a and five beacons from group 102b). In other instances, the monitored beacons 103 only includes beacons from the group 102a (e.g., twenty beacons from group 102a). The variation in the individual beacons that are included within the monitored beacons 103 may be attributable to, for example, the technique used by the mobile device 110 to monitor a threshold number of beacons when a larger number of beacons are potentially detectable (e.g., have a broadcast range that includes a current position of the mobile device 110).

Referring now to steps (2) and (3), which are depicted in FIG. 2 using labels "2" and "3," respectively, once movement for the mobile device 110 (e.g., from position A in a direction towards position B) has been detected, the obtained beacon broadcast data 104a for the monitored beacons 103 is included within the beacon proximity data 104b, which is then transmitted to the application server 120 over the network 105. The beacon proximity data 104b can include, for example, unique identifiers for each of the individual beacons of the monitored beacons 103. The beacon proximity data 104b can also include a location identifier that identifies the particular position in which mobile device 110 is presently located.

The beacon proximity data 104b also include movement data detected by the mobile device 110 when located at the position A. For example, as described above, location data can include, sensor data indicating a direction of movement (e.g., based on compass data collected by the mobile device 110), a rate of travel (e.g., based on accelerometer data), among other types of movement information. The movement data can be used to indicate a rate of change in the position of the mobile device 110 in relation to an initial position (e.g., position A) in order to estimate an updated position (e.g., position B). In some implementations, the movement data can also be ascertained based on detected connection events with certain designated beacons that have very small broadcast ranges such that the detection of a connection event between the mobile device 110 and the designated beacons can be used to that the mobile device 110 was nearby the designated beacon. The beacons A18 and B15 illustrated in FIG. 1 can represent examples of designated beacons. As the mobile device 110 moves between position A and position B, connection events between the mobile device 110 and the beacons A18 and B15 within the indicated waypoint of movement can be used to estimate the direction of travel relative to the position A in order to predict that the updated position of the mobile device 110 will be position B at some later point in time.

In some implementations, the transmitted beacon proximity data 104b can include other types of data detected by the mobile device 110 in relation to connection events with individual beacons within the monitored beacons 103. For instance, the beacon proximity data 104b can include signal connection strengths for each of the beacons within the monitored beacons 103. The signal connection strengths can be descriptive of a predicted distance between the mobile device 110 and a corresponding beacon. As an example, a mobile device 110 can detect connection events with the twenty beacons that are monitored by the mobile device when located in position A. Each of these twenty beacons can be associated with the same geographical area within a location (e.g., a department within a store) and physically arranged such that when the mobile device 110 is in a particular position within the geographical area (e.g., position A), each of the twenty that are being monitored by the mobile device 110 are in different directions relative to position of the mobile device 110. (e.g., North, West, and South West). In this example, beacons that are further away can be detected to have a lower signal strength compared to beacons that are closer to the mobile device 110. Thus, the detected signal strengths can be used to indicate how far individual beacons are placed in relation to a particular position of the mobile device 110.

Referring now to step (4), which is depicted in FIG. 2 using the label "4," once the beacon proximity data 104b is transmitted to the server 120, the server 120 then processes the received data in relation to stored beacon data 122 and stored application content data 124. The server 120 compares the data included within the beacon proximity data 104b (e.g., identification information for each of the monitored beacons 103), movement data associated with the mobile device 110, and reference information for all beacons within the location stored within the beacon data 122. The comparison can be used to identify (i) a particular set of beacons for the mobile device 110 to monitor when located at an updated position (e.g., position B), and (ii) application content related to products physically placed at the position B that are associated with the particular set of beacons.

In the first instance, the server 120 identifies the particular set of beacons by cross-referencing the identification information for the monitored beacons 103 (indicating the beacons that were being monitored by the mobile device 110 when located in the position A), and reference beacon arrangement information that indicates how the detected beacons 103 are arranged in relation to all beacons within the location. In the second instance, having identified the particular set of beacons, the server 120 then utilizes content mappings indicated within a repository 310 stored within the beacon data 122 in order to identify the content associated with the particular set of beacons.

In the example depicted, the server 120 identifies more appropriate set of beacons for the mobile device 110 to monitor given the movement data included within the beacon proximity data 104b. For example, because mobile device 110 moves toward the top right portion of the building, the server 120 determines that it is more optimal for the mobile device 110 to monitor beacons B13 and B14, which are indicated in the predetermined array to be closer to the position B relative to beacons A18 and A13. Thus, in this example, the server 120 generates a monitoring instruction 104d that instructs the mobile device 110 to stop monitoring beacons A18 and A13, and start monitoring beacons B13 and B14. In addition, because the repository 310 specifies that beacons B1-B28, including the beacons B13 and B14, are both associated with "MEN'S SHOES" and "NEW ARRIVALS," the server 120 generates application content 104c to include this content from the application content data 124.

The server 120 can also, for example, identify a location identifier (e.g., descriptive alphanumeric "4FKIDSSPORT," or non-descriptive, purely numeric "114549") included within the beacon proximity data 104b in order to determine a location (e.g., "fourth floor kids sporting goods department") for which beacon data should be processed. In addition, the server 120 can also identify the beacon identifiers included within the beacon proximity data 104b in order to identify the group of beacons 103.

The beacon data 122 can include data related the group of beacons 103. For example, the beacon data 122 can include a predetermined beacon array indicating their physical arrangement within the location in which the mobile device 110 is presently located. As an example, multiple beacons can be placed in a grid arrangement with specified distances between each individual beacon (e.g., the arrangement of the groups of beacons 102a and 102b illustrated in FIG. 1). Other examples of physical arrangements include circular arrangements surrounding a point of interest within a location, or a linear arrangement along a straight path within a location. In each of these examples, the beacon data 122 can specify a type of physical arrangement corresponding to the group of beacons 103, and coordinate points associated with each individual beacon identifying a positioning of each individual beacon within the physical arrangement.

The application content data 124 can include various types of electronic content that may be of interest to a user when he/she is physically present at the updated location of the mobile device 110 (e.g., position B). For instance, the application content data 124 can include electronic advertisements that are provided for sale in specific areas or positions within the location, information related to points of interest within the location, or notifications to display to the user when the mobile device 110 is determined to be in a particular position within the location. In one example, the location is a store that sells products for purchase and the application content data 124 includes advertisements, sales offers, notifications, and/or other types of electronic content that is related to the products that are available for purchase at the store. In another example, the location is a museum that provides different exhibits for display in different areas of the museum. In this example, the application content data 124 can include informational data that is related to each of the exhibits that are provided for display in the museum. In yet another example, the location is a convention center where a conference with different events is being held. In this example, the application content data 124 can include event information data, or other types of electronic content that are relevant to the event that is taking place near certain areas or regions within the location.

Referring now to steps (5) and (6), which are depicted in FIG. 2 using labels "5" and "6," respectively, after identifying the particular set of beacons to be monitored by the mobile device 110 and the content associated with the particular set of beacons, the server 120 transmits the application content 104c and the monitoring instruction 104d to the mobile device 110 over the network 105. As described above, the application content 104c includes content that is associated with the particular set of beacons that the server 120 determines is more likely to be relevant to the updated location of the mobile device 110 (e.g., the position B) based on the detected movement data of the mobile device 110. The application content 104c may include content for all or some of the particular set of beacons based on the location. For instance, in the example, the monitoring instruction is provided such that the particular set of beacons replaces the beacons A18 and A13 with the beacons B13 and B14 within the monitored beacons 103. The application content 104c, however, includes content only associated with the beacons B13 and B14 (e.g., a subset of the particular set of beacons) because the movement data indicates that content associated with other beacons in the particular set of beacons (e.g., beacons included in group 102a) such as "KID'S SHOES" are no longer relevant to the products that are placed at the physical location within the building corresponding to position B. In this example, the application content 104c thus includes only content associated with beacons B13 and B14 (e.g., "MEN'S SHOES" and "NEW ARRIVALS").

Referring now to step (7), which is depicted in FIG. 2 using the label "7," the application content 104c and the monitoring instruction 104d are received from the server 120 by the mobile device 110. The mobile device 110 then configures the monitoring of beacons in the location in accordance with the monitoring instruction 104d, and provides the content included within the application content 104c for output on the mobile device 110 through the application 112. In response, the mobile device 110 terminates prior monitoring of the beacons A18 and A13 (e.g., which was initiated when located in the position A), and initiates monitoring of beacons B13 and B14. In addition, the mobile device 110 also configures the application 112 provides content included within the application content 104c (e.g., information related to "MEN'S SHOES" and "NEW ARRIVALS").

As illustrated, the application 112 presents a user interface that allows the user to perceive individual beacons that are presently being monitored by the mobile device 110 after reconfiguring its monitoring in accordance with the monitoring instruction 104d (e.g., beacons B13 and B14), and associated electronic content that is included within the received application content 104c (e.g., information related to "MEN'S SHOES" and "NEW ARRIVALS"). As illustrated in FIG. 1, the electronic content can include sales discounts for shoe products that are near the present position of the mobile device 110 within the location and/or informational data indicating new shoe products that have recently arrived in the store.

In summary, the techniques described above with respect to FIGS. 1 and 2 enable the mobile device 110 to monitor new beacons (e.g., beacons B13 and B14) that were not previously included in an initial set of monitored beacons (e.g., the monitored beacons 103), and provide content associated with the two newly monitored beacons (e.g., information related to "MEN'S SHOES" and "NEW ARRIVALS") in relation to a detected movement of the mobile device 110 from position A to position B. The communications between the mobile device 110 and the server 120 therefore enable the mobile device 110 to intelligently and selectively monitor a particular set of beacons, below its specified threshold, so that beacons that are more relevant to the updated position of the mobile device 110 after it has completed its movement are monitored as opposed beacons that are still detectable when the mobile device 110 is located in the updated position, but are no longer relevant to the updated position (e.g., beacons A18 and A13).

FIGS. 3A and 3B illustrate examples of specific micro-location monitoring techniques. FIG. 3A illustrates a micro-location monitoring technique for providing different types of content when the mobile device 110 is detected in different areas of a location. FIG. 3B illustrates a micro-location monitoring technique for tracking the movement of the mobile device 110 throughout different areas of the location.

Although the examples of the stores illustrated in FIGS. 3A and 3B include placements of single beacons in geographical areas of a location for simplicity, in other implementations, geographical areas of a location may include multiple beacons placed within them. For example, there may be 140 different beacons inside of the department store. For instance, the mobile device 110 may only be capable of monitoring twenty of the 140 beacons at any instance in time. To ensure that the mobile device 110 is monitoring the appropriate beacons within the broadcast range, the micro-location monitoring techniques described throughout can be used to enable the mobile device 110 to receive information from the application server 120 as to which particular beacons to monitor at a predicted position of the mobile device 110.

In one example, if beacons are placed in such a manner that they have overlapping broadcast regions, then each of these beacons can be associated with the same electronic content such that when the mobile device 110 is located within the overlapping region, the shared content is provided for output on the mobile device 110. In another example, multiple beacons placed in the same geographical area can be configured such that they do not share overlapping broadcast regions (e.g., to prevent multiple beacon detection when the mobile device 110 is located in a specified position). For instance, the beacons may either be placed at a sufficient distance from one another, or have their broadcast powers reduced in order to decease their corresponding broadcast ranges.

Referring initially to FIG. 3A, the system 100 can use micro-location monitoring techniques to detect changes in present position of the mobile device 110 within a store 300. The detected changes can then be used to dynamically update the content that is displayed on the application 112. As described above, the dynamic updates can be provided based on communications between mobile device 110, individual beacons placed in different areas of the store 300, and the application server 120. In this regard, the dynamic updates can be used to provide users with more relevant content and/or information related to nearby products or points of interest in different areas of the store 300.

When the mobile device 110 initially enters into the store 300A through a store entrance, a present position 310a of the mobile device 110 is within a broadcast range of the beacon 302a. The beacon 302a broadcasts beacon information (e.g., the beacon broadcast data 104a) to all mobile devices that enter into the store 300. Once the mobile device 110 detects the broadcasted beacon information, a request for content that includes the detected information can then be automatically transmitted to the application server 120. The application server 120 then identifies relevant application content within the stored application content data 122 that is associated with the beacon 302a using the detected beacon broadcast information included within the received content request. The relevant application content is then provided to the mobile device 310a for output on the user interface 312a.

In the example shown, the present position 310a determined for the mobile device 110 (based on the communication event with the beacon 302a) indicates that the mobile device 310a is presently located near the entrance of the store. In response, the interface 312a displays a welcome message for the fictional store, "MEN'S SUIT FACTORY." In addition, because the location of the beacon 302a is near the entrance of the store, the interface 312a also provides general sales information that applies to all products being sold within the store 300.

When the user associated with the mobile device 110 moves to area B of the store 300A for "MEN'S CLOTHING," the system 100 then determines that a present position 310b of the mobile device 110 is within a broadcast range of a beacon 302b. In this instance, using similar techniques as described above, the application server 120 provides electronic content related to men's clothing products for output on an interface 312b of the application 112. Thus, because the beacon 302b is placed in the men's clothing department, beacon information for the beacon 302b stored within the beacon data 122 is associated with men's clothing products such as dress shirts, chinos, and khakis. Based on a detected communication event between the mobile device 110 and the beacon 302b, the application server 120 then provides electronic content associated with men's clothing for output on the application 112.

Finally, when the user associated with the mobile device 110 moves to area C of the store 300A for "MEN'S SHOES," the system 100 determines that a present position 310c of the mobile device 110 is within a broadcast range of a beacon 302c. In this instance, the application server 120 provides electronic content related to men's shoes for output on an interface 312c of the application 112. Thus, because the beacon 302c is placed in the men's shoes department, beacon information for the beacon 302c stored within the beacon data 122 is associated with men's shoes such as the most popularly purchased shoes by other others. Based on the detected communication event between the mobile device 110 and the beacon 302c, the application server 120 then provides electronic content associated with men's shoes for output on the application 112.

In each of the examples described above, respective positions of the mobile device 110 within the store 300A at different time points (e.g., positions 310a, 310b, and 320c) are inferred based on detected communication events between the corresponding beacons placed in the different areas of the store 300. As described above, because each of the beacons 302a, 302b, and 302c are associated with specific pieces of electronic content that is relevant to the physical placement of the beacons within the store (e.g., areas A, B, and C), the detected connection events can be used to provide area-specific content that is currently relevant to the user for output on the application 112.

Other examples of electronic content that can be provided to for output on the mobile application 112 include coupons, emails, gift cards, and the like, and may can also be determined by the application server 120 based on determining that the mobile device 110 has received one or more of the unique identifiers for beacons that are associated with the corresponding electronic content.

Referring now to FIG. 3B, the system 100 can use micro-location monitoring techniques to identify a pathway taken by the user associated with the mobile device 110 in navigating through a store 300B. The identified pathway can be used to determine, by either the mobile device 110 or the server 120, various parameters that are descriptive of user activity within the store 300B. As illustrated in FIG. 3B, an example of a user activity parameter can include a total amount of time spent in each area of the store 300B, which can be used to characterize a user preference for products that are available for purchase in each area of the store 300B. In another example, a user activity parameter can include an order in which a user visits particular areas of the store 300B, which can be used to identify user priorities in relation to products that are available for purchase in each area of the store 300B.

In general, the pathway taken by the user associated with the mobile device 110 can determined based on tracking the present position of the mobile device 110 over the period of time in which the mobile device 110 is located within the store 300B. As described above, communication between individual beacons within the location and the mobile device 110 can be used to estimate a present position of the mobile device 110 within a location based on known reference positions associated with each of the individual beacons within a predetermined array of beacons. For example, a detected connection event between the mobile device 110 and the beacon 302a can be used to identify a geographical area or area within the store 300B in which the mobile device 110 is presently located. Additional information, such as connection signal strengths of the detected beacons, or signals obtained from multiple beacons within the same geographical areas can then be used to estimate a specific position of the mobile device 110 within the area in which the mobile device 110 is presently located.

The techniques to estimate the position of the mobile device 110 can be performed periodically over time intervals in order to track the movement of mobile device 110 within the store 300B over a period of time. In some instances, such techniques can be performed in real-time in order to identify real-time changes to the position of the mobile device 110 based on changes to respective connection signal strengths of detected beacons within the broadcast range of the mobile device 110. For example, a diminishing connection signal strength can be used to indicate that the mobile device 110 is moving away from a particular beacon, whereas an increasing connection signal strength can be used to indicate that the mobile device 110 is moving toward a particular beacon.

In addition, measured connection signal strengths from multiple beacons placed in the same area can be used to determine a direction of movement of the mobile device 110. As an example, an area in which the mobile device 110 is located includes two beacons, a first beacon placed north of the mobile device 110 and a second beacon placed south of the mobile device 110. If the monitored connection signal strength between the mobile device and the beacons is increasing for the first beacon, but decreasing for the second beacon, then the system 100 determines that the mobile device 110 is moving north from a prior position.

In some implementations, position tracking techniques can be supplemented, augmented, or validated using other types of sensor data that are obtained independently from the communication between the mobile device 110 and the beacons placed within a location. The mobile device 110 may obtain one or more of GPS data, accelerometer data, Wi-Fi connectivity data, or other types of wireless communication data in order to independently verify the movement of the mobile device 110 throughout the store 300B. For example, GPS data can be used to identify an initial baseline position of the mobile device 110 prior a user entering an indoor location. Accelerometer data, inertial measurement data, and compass data can then be used to track changes in the baseline position based on determining a rate of motion and a direction of movement. The system 100 can then compare a predicted position determined based on the locations of beacons to a predicted position measured using the other types of sensor data to measure a correspondence between the two different measurements.

The mobile device 110 may periodically track the initiation and termination of connection events between the mobile device 110 and individual beacons as the mobile device moves throughout different areas of the store 300B. The detected connection events can then be stored in a table 310 that specifies a beacon identifier, an associated area within the store 300B, and a time point associated with the start of the connection event. For example, as depicted in FIG. 3B, the user initially moves from the store entrance to the men's clothing department between 12:03 PM and 12:04 PM, correspond to time points for the connection events between the mobile device 110 and the beacon 302a and the mobile device 110 and the beacon 302b, respectively. The user then moves toward the men's shoes department between 12:04 PM and 12:09 PM, the later of which corresponds to the connection event between the mobile device 110 and the beacon 302c. The user finally makes his/her way towards the exit of the store 300B between 12:09 PM and 12:27 PM, the later of which corresponds to the connection event between the mobile device 110 and the beacon 302a as the user exits the store 300B.

In the example described above, a comparison of time points associated with connection events can then be used to determine total times 320a and 320b that the user has spent in the men's clothing department and the men's shoes departments, respectively, of the store 300B. In particular, data within the table 310 indicates that the user spent a greater amount of time in the men's shoes department over the men's clothing department, indicating that the user may have a greater preference towards men's shoes products compared to men's clothing products. In addition, the waypoint of detected movement indicates that the user visited a larger amount of the area of the men's shoes department compared to the area visited in the men's clothing department, further indicating a greater preference towards men's shoes products compared to men's clothing products.

In other examples of retail environments, individual beacons can be grouped in various ways (e.g., twenty beacons can be grouped within the same department or spread throughout the store). In this regard, the micro-location monitoring techniques employed by the system 100 can be used to satisfy various business objectives. In addition, the arrangement of beacons within the retail environment (e.g., physical placement of the beacons in certain areas) or the configuration of the beacons and/or other supporting devices (e.g., geo-fences, Wi-Fi access points, etc.) can be adjusted over time based on a number of commercial factors. The particular micro-location techniques utilized by the system 100 can therefore be adjusted based on the particular retail environment used. In some examples, sets of beacons may be customized for particular users so as to monitor for beacons that are associated with products that are most frequently purchased by each user. In another example, sets of beacons may be tailored to different marketing campaigns/initiatives. In this example, in addition to providing for more effective consumer marketing and tracking, techniques can also be used enable the determination enhanced business analytics as illustrated in FIG. 3B. Other information relating to a particular store and the user can also be used by the system 100 in conjunction with data provided by these techniques to derive granular insights associated with consumer habits and trends. Such data can be further used as feedback in order to dynamically adjust beacon groupings and achieve different business objectives.

Figure 4:
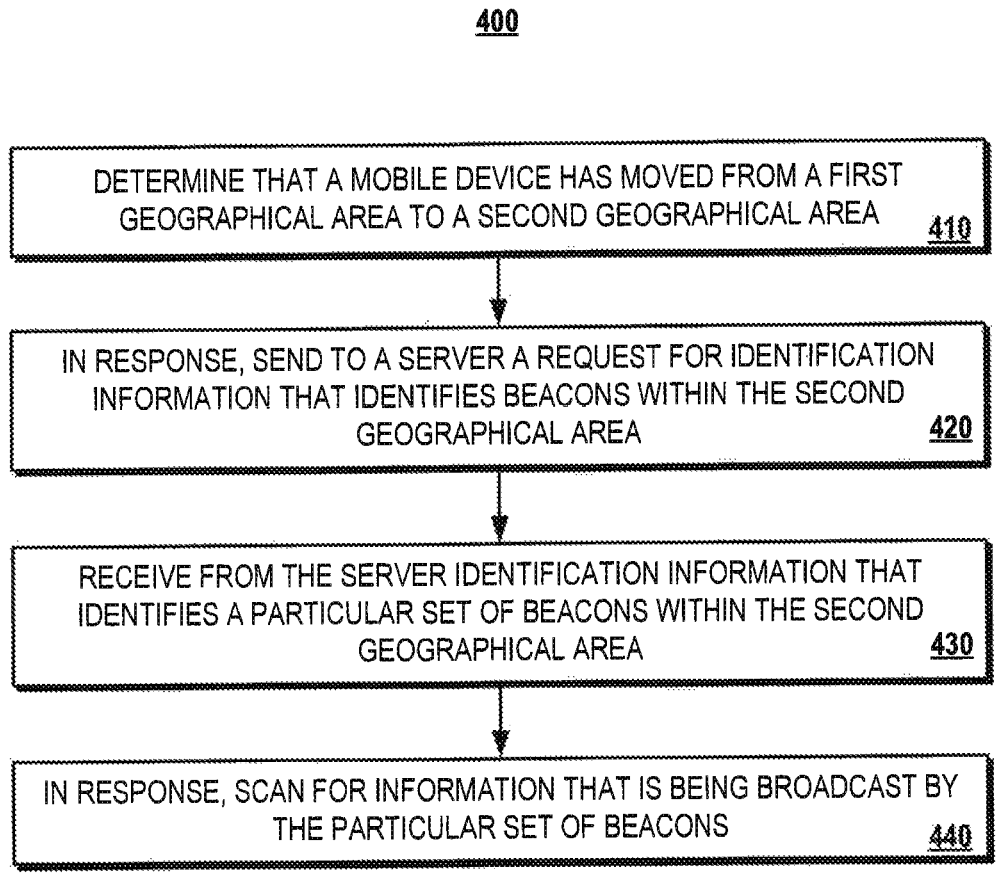
FIG. 4 illustrates an example of a process for monitoring changes to a micro-location for a mobile device.

FIG. 4 illustrates an example of a process 400 for monitoring changes to micro-locations associated with a mobile device. Briefly, the process 400 can include determining that a mobile device has moved from a first geographical area to a second geographical area (410), sending a request to a server for a list of beacons associated with the second geographical area (420), receiving a list of a particular set of beacons from the server (430), and scanning for information that is being broadcast by the particular set of beacons (440).

In more detail, the process 400 can include determining that a mobile device has moved from a first geographical area to a second geographical area (410). For instance, as described above with respect to FIG. 1, the mobile device 110 may determine that it has moved from a geographical area associated with the collection of beacons 102a to a geographical area associated with the collection of beacons 102b. This determination can be based on a variety of factors as described above. In some implementations, the determination is based on identifying connection events with individual beacons that are between the two geographical areas such as beacons 1 and 2 illustrated in FIG. 1.

In some implementations, the determination that the mobile device 110 has moved can be augmented and/or adjusted using other types of sensor data that indicate a location and/or movement of the mobile device 110 (e.g., GPS data, Wi-Fi connectivity data, cellular network data, accelerometer data, magnetic fields, etc.). For example, GPS data can be used to determine a present position of the mobile device within a geographical area of the location, and accelerometer data can be used to determine a predicted direction of movement of the mobile device within the geographical area. In this example, the initial position indicated by the GPS data, along with the direction of movement and the connection event data can be used to precisely identify a movement of the mobile device 110 between geographical areas.

In some implementations, in addition to determining that the mobile device 110 has moved between geographical areas within the location, the mobile device 110 may also precisely identify a change in position of the mobile device 110 (e.g., a change from an initial position within the geographical area associated with the group of beacons 102a to an updated position within the geographical area associated with the group of beacons 102b). In such implementations, the mobile device 110 may determine a predicted position within the new geographical area based on respective signal connection strengths for beacons within the geographical area. For example, as described above, a stronger signal strength can be used to indicate that the mobile device 110 is closer to a particular beacon, whereas a weaker signal strength can be used to indicate that the mobile device 110 is farther from another beacon.

The process 400 can include sending a request to a server for a set of beacons associated with the second geographical area (420). For instance, the mobile device 110 may send a request for a list of beacons associated with the second geographical area (e.g., the geographical associated with the collection of beacons 102b) to the application server 120. As described above with respect to FIG. 2, the request can include beacon proximity data 102b for the collection of beacons 102b based on connection events with the mobile device 110. In some implementations, the request may include other types of information that enables the application server 120 to predict an updated position of the mobile device 110, and the beacons within the collection of beacons 102b that are closest to the mobile device 110.

The process 400 can include receiving a list of a particular set of beacons from the server (430). For instance, the mobile device 110 may receive a list of a particular set of beacons from the application server 120. As described above with respect to FIG. 2, the particular set of beacons can represent one or more beacons from among the group of beacons 102b that are determined to be within a proximity to the mobile device 110 (e.g., beacons that are closes to the mobile device 110 within a new geographical area that the mobile device 110 has moved to).

In some implementations, the mobile device 110 may obtain data associated with the particular set of beacons from the application server 120. For example, as illustrated in FIG. 2, the mobile device 110 may receive application content 104c associated with the particular set of beacons. The application content 104c can specify, for example, electronic content from the stored application content 124 that is mapped to the particular set of beacons within the stored beacon data 122. In addition, the application content 104c can also include beacon information stored within the beacon data 122. For example, the beacon information can include a physical arrangement of the particular set of beacons that were included in the request sent to the application server 120.

The process 400 can include scanning for information that is being broadcast by the particular set of beacons (440). For instance, the mobile device 110 may scan for information that is being broadcast by the particular set of beacons in response to receiving data from the application server 120. As described above, in some implementations, the mobile device 110 may obtain electronic content associated with beacons that are determined to be nearby a predicted position of the mobile device 110 within a new geographical area that the mobile device 110 has moved to. In such implementations, the obtained electronic content can be content that is relevant to products that are available for purchase nearby the predicted location of the mobile device 110.

In some implementations, the mobile device 110 may selectively enable monitoring of some beacons while selectively disabling monitoring of other beacons in order to ensure that the total number of beacons monitored by the mobile device 110 is below a specified threshold for the mobile device 110. For instance, referring to the example illustrated in FIG. 1, in response to determining that the mobile device has moved from a geographical area associated with the collection of beacons 102a to a geographical area associated with the collection of beacons 102b, the mobile device may disable existing wireless monitoring of one or more beacons within the collection of beacons 102a and also enable existing monitoring of one or more beacons within the particular set of beacons identified by the server and also included within the collection of beacons 102b. In this example, monitoring of beacons within the group of beacons 102a is disabled since the movement of the mobile device 110 has changed its position such that the content associated with the beacons in this group are no longer relevant to the updated position of the mobile device 110.

Figure 5:
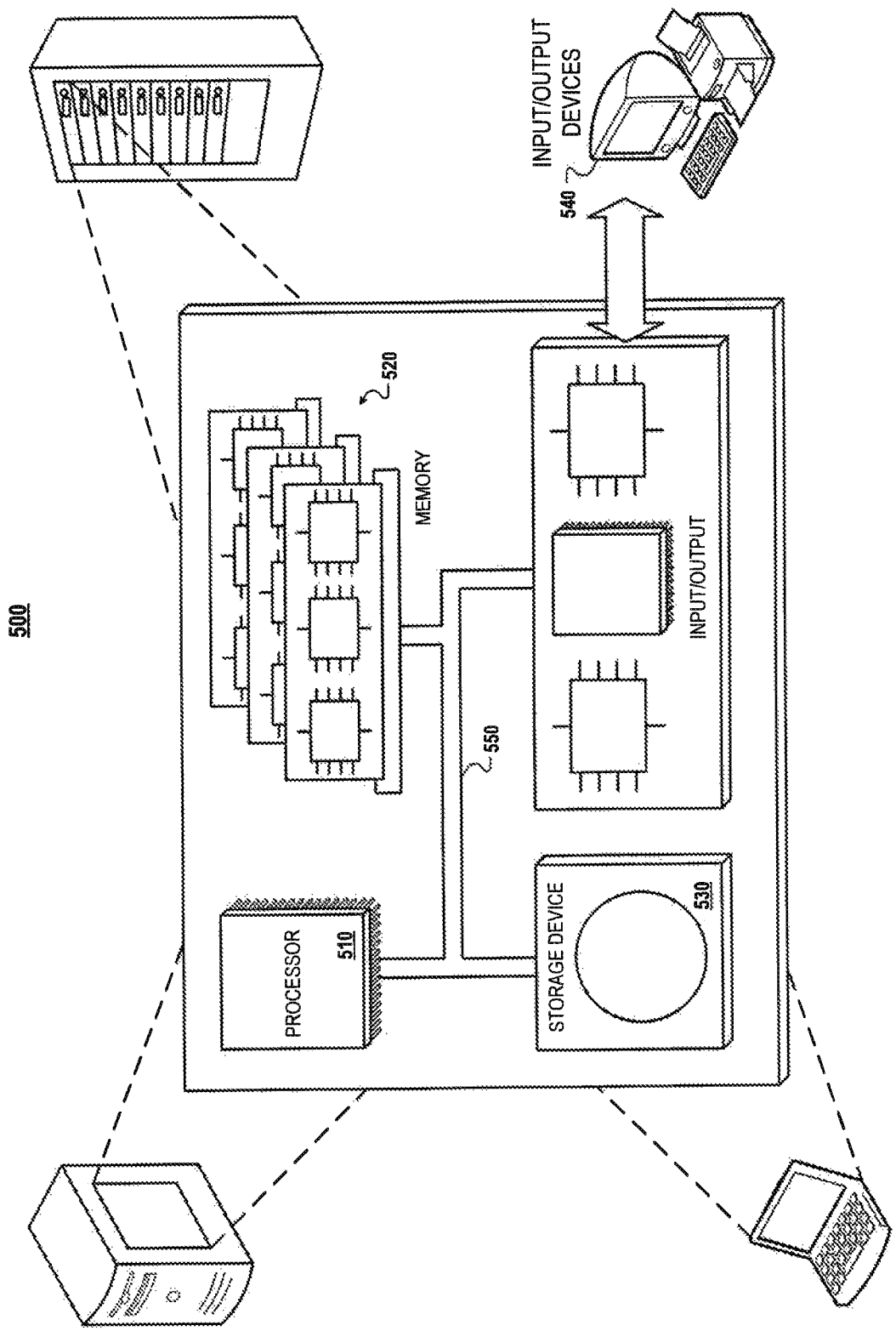
FIG. 5 is a schematic diagram of an example of a generic computer system.

FIG. 5 is a schematic diagram of an example of a computer system 500. The system 500 can be used for the operations described in association with FIG. 1 according to some implementations. The system 500 may be included in the system 100.

The system 500 includes a processor 510, a memory 550, a storage device 530, and an input/output device 540. Each of the components 510, 550, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 550 or on the storage device 530 to display graphical information for a user interface on the input/output device 540.

The memory 550 stores information within the system 500. In one implementation, the memory 550 is a computer-readable medium. In one implementation, the memory 550 is a volatile memory unit. In another implementation, the memory 550 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of the disclosure. Accordingly, other implementations are within the scope of the following claims.

What is claimed is:

1. A computer-implemented method comprising:
   determining, by a mobile device, that the mobile device has moved to a geographical area;
   providing, by the mobile device and to a server, a first indication that the mobile device has moved to the geographical area;
   receiving, by the mobile device from the server, data indicating (i) identification information for a set of beacons located within the geographical area and (ii) a physical arrangement of the set of beacons within the geographical area;
   configuring, by the mobile device and based on the physical arrangement of the set of beacons, wireless monitoring of connection events such that monitoring of one or more beacons included in the set of beacons is disabled;
   identifying, by the mobile device and based on the identification information, a beacon from among the set of beacons that is closest to the mobile device and is not included in the one or more beacons for which monitoring of connection events has been disabled;
   establishing, by the mobile device, a connection to the beacon that is identified as being the closest to the mobile device;
   providing, by the mobile device and to the server, a second indication that the mobile device has established a connection to the beacon;
   receiving, by the mobile device and from the server, data indicating a particular type of content identified by the server to be associated with the beacon based at least on the second indication; and
   providing, for output on the mobile device, the particular type of content.

2. The method of claim 1, further comprising:
   obtaining, by the mobile device, sensor data indicating respective signal connection strengths for one or more beacons that are associated with the geographical area and are currently being monitored by the mobile device; and
   determining a predicted position for the mobile device within the geographical area based at least on the respective signal connection strengths for the one or more beacons that are associated with the geographical area and are being currently monitored by the mobile device.

3. The method of claim 1, further comprising:
   in response to determining that the mobile device has moved to the geographical area:
   disabling, by the mobile device, existing wireless monitoring of one or more beacons that are associated with a previous geographical area; and
   enabling, by the mobile device and based on the identification information, wireless monitoring of the set of beacons such that a total number of beacons being monitored by the mobile device is below a threshold number of beacons for the mobile device.

4. The method of claim 1, wherein determining that the mobile device has moved to the geographical area comprises:
   determining that the mobile device has exited a geographical boundary specified by a first geo-fence associated with a first geographical area; and
   determining that the mobile device has entered a geographical boundary specified by a second geo-fence associated with the geographical area.

5. The method of claim 1, further comprising:
   after determining that the mobile device has moved to the geographical area, identifying one or more beacons, from among the set of beacons, that are within a physical proximity to a predicted position of the mobile device within the geographical area;
   determining, for at least one of the one or more beacons, a time period for which the one of the one or more beacon remains within the physical proximity to the predicted position of the mobile device within the geographical area.

6. The method of claim 1, wherein the set of beacons is selected by the server from among multiple beacons located within the geographical area.

7. The method of claim 1, wherein the set of beacons includes a number of beacons less than or equal to a threshold number of available beacon connections of the mobile device.

8. A system comprising:
   one or more computers; and
   a non-transitory storage device storing computer-executable instructions that, when executed by the one or more computers, causes the one or more computers to perform operations comprising:
   determining, by a mobile device, that the mobile device has moved to a geographical area;

providing, by the mobile device and to a server, a first indication that the mobile device has moved to the geographical area;

receiving, by the mobile device from the server, data indicating (i) identification information for a set of beacons located within the geographical area and (ii) a physical arrangement of the set of beacons within the geographical area;

configuring, by the mobile device and based on the physical arrangement of the set of beacons, wireless monitoring of connection events such that monitoring of one or more beacons included in the set of beacons is disabled;

identifying, by the mobile device and based on the identification information, a beacon from among the set of beacons that is closest to the mobile device and is not included in the one or more beacons for which monitoring of connection events has been disabled;

establishing, by the mobile device, a connection to the beacon that is identified as being the closest to the mobile device;

providing, by the mobile device and to the server, a second indication that the mobile device has established a connection to the beacon;

receiving, by the mobile device and from the server, data indicating a particular type of content identified by the server to be associated with the beacon based at least on the second indication; and providing, for output on the mobile device, the particular type of content.

9. The system of claim 8, wherein the operations further comprise:

obtaining, by the mobile device, sensor data indicating respective signal connection strengths for one or more beacons that are associated with the geographical area and are currently being monitored by the mobile device; and determining a predicted position for the mobile device within the geographical area based at least on the respective signal connection strengths for the one or more beacons that are associated with the geographical area and are being currently monitored by the mobile device.

10. The system of claim 8, wherein the operations further comprise in response to determining that the mobile device has moved to the geographical area:

disabling, by the mobile device, existing wireless monitoring of one or more beacons that are associated with a previous geographical area; and enabling, by the mobile device and based on the identification information, wireless monitoring of the set of beacons such that a total number of beacons being monitored by the mobile device is below a threshold number of beacons for the mobile device.

11. The system of claim 8, wherein determining that the mobile device has moved to the geographical area comprises:

determining that the mobile device has exited a geographical boundary specified by a first geo-fence associated with a first geographical area; and determining that the mobile device has entered a geographical boundary specified by a second geo-fence associated with the geographical area.

12. The system of claim 8, wherein the operations further comprise:

after determining that the mobile device has moved to the geographical area, identifying one or more beacons, from among the set of beacons, that are within a physical proximity to a predicted position of the mobile device within the geographical area;

determining, for at least one of the one or more beacons, a time period for which the one of the one or more beacon remains within the physical proximity to the predicted position of the mobile device within the geographical area.

13. The system of claim 8, wherein the set of beacons is selected by the server from among multiple beacons located within the geographical area.

14. The system of claim 8, wherein the set of beacons includes a number of beacons less than or equal to a threshold number of available beacon connections of the mobile device.

15. At least one non-transitory storage device storing computer-executable instructions that, when executed by the one or more computers, causes the one or more computers to perform operations comprising:

determining, by a mobile device, that the mobile device has moved to a geographical area;

providing, by the mobile device and to a server, a first indication that the mobile device has moved to the geographical area;

receiving, by the mobile device from the server, data indicating (i) identification information for a set of beacons located within the geographical area and (ii) a physical arrangement of the set of beacons within the geographical area;

configuring, by the mobile device and based on the physical arrangement of the set of beacons, wireless monitoring of connection events such that monitoring of one or more beacons included in the set of beacons is disabled;

identifying, by the mobile device and based on the identification information, a beacon from among the set of beacons that is closest to the mobile device and is not included in the one or more beacons for which monitoring of connection events has been disabled;

establishing, by the mobile device, a connection to the beacon that is identified as being the closest to the mobile device;

providing, by the mobile device and to the server, a second indication that the mobile device has established a connection to the beacon;

receiving, by the mobile device and from the server, data indicating a particular type of content identified by the server to be associated with the beacon based at least on the second indication; and providing, for output on the mobile device, the particular type of content.

16. The non-transitory storage device of claim 15, wherein the operations further comprise:

obtaining, by the mobile device, sensor data indicating respective signal connection strengths for one or more beacons that are associated with the geographical area and are currently being monitored by the mobile device; and determining a predicted position for the mobile device within the geographical area based at least on the respective signal connection strengths for the one or more beacons that are associated with the geographical area and are being currently monitored by the mobile device.

17. The non-transitory storage device of claim 15, wherein the operations further comprise in response to determining that the mobile device has moved to the geographical area:

disabling, by the mobile device, existing wireless monitoring of one or more beacons that are associated with a previous geographical area; and enabling, by the mobile device and based on the identification information, wireless monitoring of the set of beacons such that a total number of beacons being monitored by the mobile device is below a threshold number of beacons for the mobile device.

18. The non-transitory storage device of claim 15, wherein determining that the mobile device has moved to the geographical area comprises:

determining that the mobile device has exited a geographical boundary specified by a first geo-fence associated with a first geographical area; and determining that the mobile device has entered a geographical boundary specified by a second geo-fence associated with the geographical area.

19. The non-transitory storage device of claim 15, wherein the operations further comprise:

after determining that the mobile device has moved to the geographical area, identifying one or more beacons, from among the set of beacons, that are within a physical proximity to a predicted position of the mobile device within the geographical area;

determining, for at least one of the one or more beacons, a time period for which the one of the one or more beacon remains within the physical proximity to the predicted position of the mobile device within the geographical area.

20. The non-transitory storage device of claim 15, wherein the set of beacons is selected by the server from among multiple beacons located within the geographical area.

* * * * *